United States Patent [19]

Koide et al.

[11] 4,328,212

[45] May 4, 1982

[54] NOVEL ANTIBIOTIC NCS-C AND PREPARATION METHOD OF THE SAME

[75] Inventors: Yoshio Koide, Tokyo; Kiyoto Edo, Miyagi; Nakao Ishida, Sendai, all of Japan

[73] Assignee: Kayaku Antibiotic Research Co., Ltd., Tokyo, Japan

[21] Appl. No.: 173,016

[22] Filed: Jul. 28, 1980

[30] Foreign Application Priority Data

Oct. 9, 1979 [JP] Japan .............................. 54/130181

[51] Int. Cl.³ .............................................. A61K 35/00
[52] U.S. Cl. .................................... 424/118; 435/169
[58] Field of Search ......................... 424/118; 435/169

[56] References Cited

FOREIGN PATENT DOCUMENTS 42-21752 10/1967 Japan .
47-680 1/1972 Japan .
54-13516 5/1979 Japan .

OTHER PUBLICATIONS

Napier et al., Biochemical and Biophysical Research Communications, 89 (2) pp. 635–642 (1979).

*Primary Examiner*—Jerome D. Goldberg
*Attorney, Agent, or Firm*—Oblon, Fisher, Spivak, McClelland & Maier

[57] ABSTRACT

The specification describes novel antibiotic NCS-C and its free acid salts. Their antimicrobial effects are at least comparative with neocarzinostatin, and, against some microorganisms, superior. The novel antibiotic NCS-C or its free acid salt is prepared either by culturing an NCS-C yielding microorganism belonging to the Streptomyces family in a culture medium, separating the culture medium into bacterial bodies and culture filtrate, and extracting the culture filtrate with a water-immiscible polar organic solvent under acidic conditions, or by decomposing neocarzinostatin under acidic conditions and extracting resultant free acid salt with a polar organic solvent.

1 Claim, 2 Drawing Figures

NOVEL ANTIBIOTIC NCS-C AND PREPARATION METHOD OF THE SAME

BACKGROUND OF THE INVENTION

The present invention relates to novel antibiotic NCS-C and a preparation method of the same.

It has already been known that high molecular antibiotics neocarzinostatin (see Japanese Patent Publication No. 21752/1967 published Oct. 26, 1967), N-1 fraction, N-2 fraction (see Japanese Patent Publication No. 680/1972 published Jan. 10, 1972) and Ma fraction (see Japanese Patent Publication No. 13516/1979 published May 31, 1979) are obtained by culturing Streptomyces carzinostaticus variant F41 Kuroya. The present inventors have extended further investigations on the cultured substance and found that it also contains a novel antibiotic NCS-C which is different in physical and chemical characteristics from neocarzionostatin, the N-1 fraction, N-2 fraction and Ma-fraction.

SUMMARY OF THE INVENTION

Accordingly, a primary object of this invention is to provide novel antibiotic NCS-C (hereinafter referred to as the NCS-C substance) and its free acid salts.

Another object of this invention is to provide a novel method for preparing novel antibiotic NCS-C and its free acid salts.

In one aspect of this invention, there is provided antibiotic NCS-C. Its hydrochloric acid salt has the following physical and chemical characteristics:
(a) appearance: light yellowish-brownish powder
(b) decomposition point: 125° C.
(c) specific rotation: $[\alpha]_D^{20} = -171°$ (c=1.4×10$^{-3}$, in methanol)
(d) elementary analysis: C 51.72, H 4.94, N 2.03, O 31.00, Cl 10.31
(e) molecular weight: 686.5–688.5
(f) molecular formula: $C_{30}H_{33-35}Cl_2NO_{13}$
(g) ultraviolet absorption spectrum: shoulders at 240, 274, 290, 305, and 330 nm
(h) infrared absorption spectrum: absorptions at 3400, 1780, 1610, 1400, 1190, 1080 and 1010 cm$^{-1}$
(i) color reactions: permanganate reaction, diazo coupling reaction-positive; xanthoprotein reaction, Ehrich reaction, Ninhydrin reaction, orcinol reaction, Molisch reaction-negative
(j) solubility: readily soluble in methanol, ethanol, propanol, and butanol; soluble in acetone; and slightly soluble in ethyl acetate; hardly soluble in water, ether and benzene.

Free acid salts of antibiotic NCS-C are also provided in accordance with this invention.

In another aspect of this invention, there is provided a method for preparing the NCS-C substance or its free acid salt. The method comprises culturing an NCS-C yielding microorganism belonging to the Streptomyces family in a culture medium; separating the culture medium into bacterial bodies and culture filtrate; and extracting the culture filtrate with a water-immiscible polar organic solvent under acidic conditions.

In a further aspect of this invention, there is also provided a method for preparing the NCS-S substance or its free acid salt. The method comprises decomposing neocarzinostatin under acidic conditions to form a free acid salt of the NCS-C substance and extracting said salt with a polar organic solvent.

DETAILED DESCRIPTION OF THE PREFERRED EMBODIMENTS OF THE INVENTION

The NCS-C substance according to this invention can be prepared, for example, as follows:

A neocarzinostatin yielding microorganism, which belongs to the Streptomyces family, is employed for the preparation of the NCS-C substance according to this invention. Among such neocarzinostatin yielding microorganisms, there are Streptomyces carzinostaticus variant F41 Kuroya and its mutants as well as all bacteria which yield the NCS-C substance and belong to the Streptomyces family. Streptomyces carzinostaticus variant F41 Kuroya has already been deposited under an acceptance number of 2257 at the Fermentation Research Institute, Agency of Industrial Science and Technology and also under ATCC No. 15945 at the American Type Culture Collection.

The culturing methods disclosed in the abovedescribed Japanese Patent Publication Nos. 21752/1967 and 13516/1979 may be followed to culture Streptomyces carzinostaticus variant F41 Kuroya for preparing the NCS-C substance according to this invention.

The NCS-C substance can be collected from the culture solution in accordance with a method which will be described below. First of all, upon the separation of the culture solution into the bacterial bodies and culture solution in accordance with a known method such as filtration or centrifugal separation, the NCS-C substance is mainly contained in the filtrate of the culture solution. The pH of the thus-obtained filtrate is then adjusted to 1–4 with a mineral acid such as hydrochloric acid or sulfuric acid, or an organic acid such as acetic acid or formic acid. Upon extracting the thus pH-adjusted filtrate with a water-immiscible solvent such as butanol or chloroform, most of the NCS-C substance moves to the organic layer. The organic layer is then concentrated and subjected to a purification step which comprises in combination adsorption chromatography such as silica gel, alumina or Amberlite XAD, reversed phase chromatography, such as μ-bondapack $C_{18}$ or Lichrosorb RP-8, and gel permiation chromatography such as Sephadex LH-20 or TSK gel. The NCS-C substance has now been obtained.

The NCS-C substance may also be obtained by decomposing, under mild conditions, purified neocarzinostatin. In other words, when neocarzinostatin powder is suspended and stirred under acidic conditions in a polar organic solvent such as methanol, ethanol, propanol, butanol, acetone, or chloroform, it is decomposed into the NCS-C substance, which is dissolved into the organic solvent, and insoluble preneocarcinostatin (described in "Journal of Antibiotics", Vol. 27, Page 766). The NCS-C substance contained in the organic solvent is then purified in accordance with the method described above.

Figure 1:
FIG. 1 is an ultraviolet absorption spectrum of the antibiotic NCS-C substance according to this invention.
Figure 2:
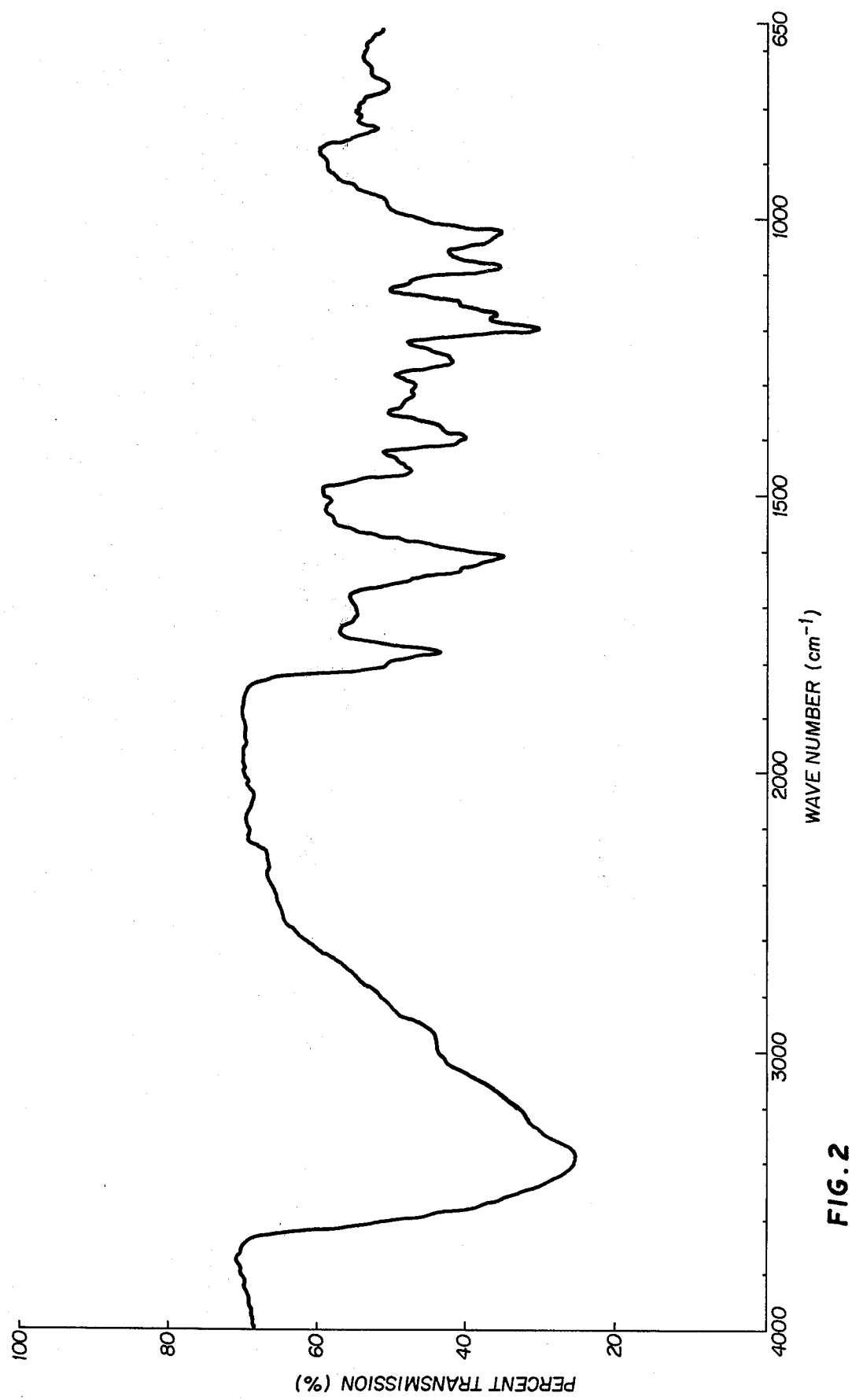
FIG. 2 is an infrared absorption spectrum of the same substance.

Thus, the NCS-C substance is obtained as an acid salt, which may be converted to the NCS-C substance per se in accordance with any suitable method known per se in the art, for example, by subjecting said acid salt to a hydrolysis reaction. Its hydrochloric acid salt has the following characteristics:

(1) physical and chemical properties:
  (a) appearance: light yellowish-brownish powder
  (b) decomposition point: 125° C.
  (c) specific rotation: $[\alpha]_D^{20} = -171°$ (c) = $1.4 \times 10^{-3}$, in methanol)
  (d) elementary analysis: C 51.72, H 4.94, N 2.03, O 31.00, Cl 10.31
  (e) molecular weight: 686.5–688.5
  (f) molecular formula: $C_{30}H_{33-35}Cl_2NO_{13}$
  (g) ultraviolet absorption spectrum (FIG. 1): shoulders at 240, 265, 274, 290, 305, and 330 nm
  (h) infrared absorption spectrum (FIG. 2): absorptions at 3400, 1780, 1610, 1400, 1190, 1080 and 1010 $cm^{-1}$
  (i) color reactions: permanganate reaction, diazo coupling reaction-positive; xanthoprotein reaction, Ehrlich reaction, Ninhydrin reaction, orcinol reaction, Molisch reaction-negative
  (j) solubility: readily soluble in methanol, ethanol, propanol, and butanol; slightly soluble in ethyl acetate; hardly soluble in water, ether and benzene.
  (k) stability: thermal stability: 60° C.

|  | 0 min. | 10 min. | 30 min. | 60 min. |
|---|---|---|---|---|
| remainder (%) | 100 | 84.4 | 72.4 | 56.9 | ultraviolet ray: irradiated by a Toshiba sterilization lamp from 20 cm away

|  | 0 min. | 10 min. | 30 min. | 60 min. |
|---|---|---|---|---|
| remainder (%) | 100 | 56.9 | 22.7 | 7.2 | pH: after the lapse of 4 hours

|  | pH 2 | pH 4 | pH 6 | pH 8 | pH 10 |
|---|---|---|---|---|---|
| remainder (%) | 100 | 100 | 55.1 | 18.9 | 0.0 |

(2) acute toxity:
  mouse intravenous injection $LD_{50} = 1.8$ mg/kg
  mouse intraperitoneal injection $LD_{50} = 10$ mg/kg and up (3) biological properties:
  (i) antitumor effects:
    Yoshida sarcoma (ip-ip)

|  | maximum tolerated dose (mg/kg) | minimum effective dose (mg/kg) |
|---|---|---|
| NCS-C substance | >10 | 0.1 |
| NCS-C substance: preneocarzinostatin (1:10) | 0.5 | 0.005 |
| Preneocarzinostatin | >10 | >10 |

Hela-S3 cells
  The NCS-C substance did not exhibit its antitumor effects in a concentration of 1.0 mg/ml, but a mixture of preneocarzinostatin and NCS-C substance (10:1) showed antitumor effects in a concentration of 0.1 mg/ml.

| Test microorganisms | minimum inhibitory concentration (mcg/ml) | | |
|---|---|---|---|
|  | NCS-C substance | NCS-C substance containing 10γ/ml of preneocarzinostatin | preneocarzinostatin |
| Proteus vulgaris OX-19 | >100 | >100 | >100 |
| Proteus morganii IFO 3848 | 100 | 100 | >100 |
| Proteus rettgeri | >100 | >100 | >100 |
| Salmonella typhi V 1901 | >100 | >100 | >100 |
| Shigella flexneri 2a | 100 | 100 | >100 |
| Shigella sonnei | >100 | >100 | >100 |
| Excherichia coli NIHJ | >100 | >100 | >100 |
| Psedomonas aeruginosa GN 83 | >100 | >100 | >100 |
| Serratia marcescens IFO 1022 | >100 | >100 | >100 |
| Staphylococcus aureus FDA 209p | 50 | 1.56 | >100 |
| Staphylococcus epidermidis IFO 3726 | 25.0 | 0.4 | >100 |
| Streptococcus haemolyticus | 25.0 | <0.1 | >100 |
| Sarcina lutea ATCC 9341 | 12.5 | <0.1 | >100 |
| Bacillus subtilis PCI 219 | 25.0 | 0.8 | >100 |
| Bacillus cereus IFO 3001 | 100 | 0.8 | >100 |
| Xanthomonas oryzae IAM 1657 | >100 | >100 | >100 |
| Candida albicans YU 1200 | >100 | >100 | >100 |

As apparent from the above tables, although the NCS-C substance according to this invention itself has antimicrobial effects, its effectiveness is considerably increased by using it in conjunction with preneocarzinostatin.

As described above, the physical, chemical and biological properties of the NCS-C substance according to the present invention are entirely different from those of neocarzinostatin produced by Streptomyces carzinostaticus variant F41 Kuroya, the N-1 fraction, N-2 franction, Ma fraction and carzinostatin complex produced by an analogous bacterium specie, Streptomyces carzinostaticus (see Japanese Patent Publication No. 5400/1960) as well as any other antibiotic. Therefore, the NCS-C substance according to this invention has now been recognized as a novel substance.

Now, the present invention will be described by means of the following examples:

EXAMPLE 1

In a 400 l culture tank, 200 l of a culture medium (adjusted to pH 6.6) having a composition of 2.0% starch, 2.0% soy bean meal, 0.5% dry yeast, 0.25% sodium chloride, 0.35% carcium carbonate, 0.005% manganese chloride, 0.005% copper sulfate and 0.005% zinc sulfate was prepared. The culture medium was thermally sterilized at 120° C. for 30 minutes. Then, 3 l of a seed solution of Streptomyces carzinostaticus variant F41 Kuroya, which had previously been cultured for 24 hours on a culture medium of the indentical composition to the above culture medium, was charged into the culture tank. The culture medium was then subjected to a 50 hour culturing at 27° C. under aeration and agitation conditions (air fed: 300 l/min.; agitation: 180 revolutions/minute). One hundred eighty liters (180 l) of a culture solution was obtained. This culture solution was then filtered by means of a filter press. After adjusting the pH of the filtrate with hydrochloric acid to pH 2.0, 100 l of n-butanol was added, and the resulting solution mixture was stirred for 2 hours at an agitation rate of 180 revolutions per minute, followed by allowing the same to stand for 24 hours. Thereafter, the butanol layer, which had been sufficiently separated from the water layer, was removed and condensed in a flash evaporator at 50° C. A concentrated solution of the NCS-C substance was obtained (yield: 1200 ml).

EXAMPLE 2

The concentrated solution obtained in Example 1 was adsorbed on a column filled with 5 l of silica gel which had previously been equilibrated with chloroform. It was then eluted with a mixture of methanol and chloroform (1:1), resulting in 400 ml of an active fraction. This fraction was then subjected to a concentration and drying step under reduced pressure. The NCS-C substance was obtained in a crude power form (yield: 2.1 g).

EXAMPLE 3

Into 50 ml of methanol was dissolved 2.1 g of the crude powder obtained in Example 2. The resulting solution was then passed through a column filled with 1 l of Sephadex LH-20 which had been equilibrated in advance with 1.0 N hydrochloric acid: methanol (1:9). It was then subjected to a chromatography by using as an elutant 1.0 N hydrochloric: methanol (1:9). Ninety milliliters (90 ml) of an active fraction was collected. It was thereafter concentrated and dried to 126 mg of the NCS-C substance powder.

EXAMPLE 4

Into 1.5 l of a 95% methanol solution was suspended 16 g of neocarzinostatin powder. After adjusting the pH of the suspension with 1 N hydrochloric acid to pH 2.0, the suspension was stirred for 2 hours and then subjected to centrifugal separation. The supernatant was then concentrated and dried to 920 mg of crude powder of the NCS-C substance. The crude powder was subjected to Sephadex LH-20 chromatography in the same manner as in Example 3. The NCS-C substance was obtained in a powder form (yield: 105 mg).

What is claimed is:

1. Antibiotic NCS-C or free acid salts thereof, the hydrochloric acid salt having the following physical and chemical characteristics:
   (a) appearance: light yellowist-brownish powder
   (b) decomposition point: 125° C.
   (c) specific rotation: $[\alpha]_D^{20} = -171°$ ($c = 1.4 \times 10^{-3}$, in methanol)
   (d) elementary analysis: C 51.72, H 4.94, N 2.03, O31.00, Cl 10.31
   (e) molecular weight: 686.5–688.5
   (f) molecular formula: $C_{30}H_{33-35}Cl_2NO_{13}$
   (g) ultraviolet absorption spectrum: shoulders at 240, 265, 274, 290, 305, and 330 nm
   (h) infrared absorption spectrum: absorptions at 3400, 1780, 1610, 1400, 1190, 1080 and 1010 $cm^{-1}$
   (i) color reactions: permanganate reaction, diazo coupling reaction-positive, xanthoprotein reaction, Ehrlich reaction, Ninhydrin reaction, orcinol reaction, Molisch reaction-negative
   (j) solubility: readily soluble in methanol, ethanol, propanol, and butanol, soluble in acetone; slightly soluble in ethyl acetate; hardly soluble in water, ether and benzene.

* * * * *